(12) United States Patent
Wedegaertner et al.

(10) Patent No.: US 9,622,723 B2
(45) Date of Patent: Apr. 18, 2017

(54) ULTRASONIC SENSOR FOR A CARDIOTOCOGRAPH TO BE USED WITHIN MAGNETIC RESONANCE TOMOGRAPHY

(75) Inventors: Ulrike Wedegaertner, Hamburg (DE); Klaus Valett, Ellerhoop (DE); Jin Yamamura, Hamburg (DE)

(73) Assignee: Ulrike Wedegaertner, Hamburg (DE)

( * ) Notice: Subject to any disclaimer, the term of this patent is extended or adjusted under 35 U.S.C. 154(b) by 991 days.

(21) Appl. No.: 13/807,944

(22) PCT Filed: Jul. 1, 2011

(86) PCT No.: PCT/EP2011/061131
§ 371 (c)(1),
(2), (4) Date: Mar. 19, 2013

(87) PCT Pub. No.: WO2012/001150
PCT Pub. Date: Jan. 5, 2012

(65) Prior Publication Data
US 2013/0178732 A1   Jul. 11, 2013

(30) Foreign Application Priority Data
Jul. 2, 2010   (DE) .................. 10 2010 025 857

(51) Int. Cl.
*A61B 8/00* (2006.01)
*A61B 8/02* (2006.01)
(Continued)

(52) U.S. Cl.
CPC ............ *A61B 8/4444* (2013.01); *A61B 5/033* (2013.01); *A61B 5/055* (2013.01); *A61B 8/02* (2013.01);
(Continued)

(58) Field of Classification Search
CPC ... A61B 5/4343–5/4362; A61B 5/0444; A61B 5/0011; A61B 8/0866; A61B 5/055
See application file for complete search history.

(56) References Cited

U.S. PATENT DOCUMENTS 3,989,034 A * 11/1976 Hojaiban ............... A61B 5/024
600/511
5,823,962 A   10/1998 Schaetzle et al.
(Continued)

FOREIGN PATENT DOCUMENTS

WO   93/08534 A1   4/1993
WO   95/02361 A1   1/1995
(Continued)

OTHER PUBLICATIONS

Kribèche et al, The Actifetus System: A Multidoppler Sensor System for Monitoring Fetal Movements, Ultrasound in Med. & Biol., vol. 33, No. 3, pp. 430-438, 2007.*
(Continued)

*Primary Examiner* — Serkan Akar
(74) *Attorney, Agent, or Firm* — Renner, Otto, Boisselle & Sklar, LLP; Grant Steyer

(57) ABSTRACT

An ultrasonic sensor according to the invention comprises at least one ultrasonic transducer, at least one resistor connected to the ultrasonic transducer and a housing accommodating the ultrasonic transducer and the resistor. The ultrasonic sensor is configured in such a way, that it is not or only slightly ferromagnetic, so that the ultrasonic sensor acts neutrally with respect to an external magnetic field (for example in an MRT).

7 Claims, 3 Drawing Sheets

(51) Int. Cl.
   *A61B 5/055*  (2006.01)
   *A61B 5/03*   (2006.01)
   *A61B 8/08*   (2006.01)
   *G01R 33/48*  (2006.01)
   *G01R 33/567* (2006.01)

(52) U.S. Cl.
   CPC .......... *A61B 8/0866* (2013.01); *A61B 8/4455* (2013.01); *A61B 8/4472* (2013.01); *G01R 33/4814* (2013.01); *G01R 33/5673* (2013.01); *A61B 2562/222* (2013.01)

(56) References Cited

U.S. PATENT DOCUMENTS

2003/0083573 A1   5/2003   Azuma et al.
2005/0272995 A1   12/2005  Prince

FOREIGN PATENT DOCUMENTS

WO   2004/026135 A1   4/2004
WO   2007/059474 A2   5/2007
WO   2008/097487 A2   8/2008

OTHER PUBLICATIONS

Gore, Hybrid Round Cable, http://www.gore.com/products/hybrid-round-cable, 2016.*
International Search Report, corresponding to PCT/EP2011/061131, completed on Sep. 21, 2011.
Written Opinion, corresponding to PCT/EP2011/061131, completed on Sep. 21, 2011.
International Preliminary Report on Patentabiliy, corresponding to PCT/EP2011/061131, issued on Jan. 8, 2013.
English translation of Written Opinion, corresponding to PCT/EP2011/061131, mailed Sep. 28, 2011.

* cited by examiner

ULTRASONIC SENSOR FOR A CARDIOTOCOGRAPH TO BE USED WITHIN MAGNETIC RESONANCE TOMOGRAPHY

FIELD OF THE INVENTION

The invention relates to an ultrasonic sensor for cardiotocography (CTG). In particular, the invention relates to a CTG ultrasonic sensor, which is usable in a magnetic resonance tomograph (MRT). Further, the invention relates to a cardiotocograph, i.e. a CTG device, having such an ultrasonic sensor as well as to a system with an MRT and a CTG device having such an ultrasonic sensor.

BACKGROUND OF THE INVENTION

Since the fetal heart is located within the uterus, the possibility of directly detecting the fetal heart frequency does not exist there, and therefore conventionally required electrocardiodiagram control while the patient holds his breath is not possible during the measurement. Therefore visualizing of anomalies of the heart and large vessels by MRI (magnetic resonance imaging) is not achievable.

For examination of a fetal heart by means of MRT, for example Manganaro et al., Prenat. Diagn. 2008, 28, 148-156, and Fogel et al., Fetal Diagn. Ther. 2005, 20, 475-480, describe True fast imaging with steady-state precision (True FISP) and real-time cine-MR-sequences to be used, whereby in these cases the procedure is carried out without control (triggering). Nijm et al., J. Magn. Reson. Imaging 2008, 28, 767-772 use self-gating (SG) algorithms for synchronization. Here among other things the low signal-to-noise ratio is limiting. Yamamura et al., Eur. Radiol. 2009, 19, 2383-90, use an invasive trigger system (Pulse wave triggering). All these methods have severe limitations, which either render their practical use on a human being impossible, or there is no yield of images of sufficient quality, which allow for evaluating anatomic structures and functional information.

Michel et al., American Journal of Roentgenologie 2003, 180, 1159-1164, come to the conclusion that fetal CTG during magnetic resonance tomography is feasible with modified standard equipment. However, it is also stated that, due to technical reasons, CTG monitoring while the patient is in the magnet is not possible (rather, measurements were made immediately after leaving the magnet). Accordingly, the study of Michel et al. provides no MRT images of the fetal heart.

The problem of interference between the CTG device and the MRT has been an unresolved problem for years.

SUMMARY OF THE INVENTION

In an embodiment of the invention, an ultrasonic sensor for a cardiotocography device (CTG device) therefore comprises at least an ultrasonic transducer, at least one resistor which is connected to the ultrasonic transducer, and a housing. The housing accommodates the ultrasonic transducer and the resistor. The ultrasonic sensor is made of materials which are nonferromagnetic, so that the ultrasonic sensor acts neutrally with respect to an external magnetic field. Specifically this means that the resistor consists of a non-ferromagnetic material and that the resistor is connected to the ultrasonic transducer through a non-ferromagnetic wire.

The ultrasonic transducer is connected to the resistor through twisted wires. More precisely, a first terminal of the ultrasonic transducer can be connected to a signal conductor of a CTG electronic system of the CTG device, and a second terminal of the ultrasonic transducer is connected through the resistor with a ground terminal of the CTG electronic system, the two wires being twisted together.

Even when the ultrasonic sensor receives signals and itself is located within the magnetic field of an MRT, there is almost no disturbance or influence on the magnetic field of the MRT, so that imaging through the MRT is possible almost without any artefacts and with the desired resolution. By way of example, the ultrasonic sensor may influence imaging in its direct proximity, without this influence being relevant to the area of interest (e.g., the fetal heart). Further, disturbances of the operation of the ultrasonic sensor by the magnetic field of the MRT and by the high-frequency impulses emitted by the MRT are avoided. Accordingly, even during ongoing measurements, the ultrasonic sensor can be operated within the imaging area of the MRT. In particular, it is possible to record Doppler-sonography signals in the MRT during ongoing MRT measurements.

In this embodiment, it may be achieved that the ultrasonic sensor is on the one hand neutral with respect to the external magnetic field, i.e., generates no disturbances in the magnetic field. On the other hand, the ultrasonic sensor is, by virtue of the connection via twisted wires, also shielded from disturbances by the by far stronger external magnetic field. This good shielding allows for a complete functionality of the ultrasonic sensor both in the static magnetic field and during the ongoing MRT measurements with irradiation of high-frequency pulses.

"Neutral" in this case may be considered to encompass that a possible disturbing field occurs only in a distance of up to 30 mm, measured perpendicularly with respect to the surface of for example the housing of the ultrasonic sensor. Preferably, a disturbing field occurs only up to a distance of 20 mm. Ideally, an external magnetic field is disturbed or influenced only in a range of distance between 0 and 12 mm.

According to an embodiment of the invention, the ultrasonic sensor has no circuit board connecting the ultrasonic transducer and the at least one resistor. In this way, an additional disturbing structure can be avoided.

According to an embodiment of the invention, the ultrasonic sensor has seven ultrasonic transducers and seven resistors, which are for example connected to each other through free wiring, preferably with twisted-pair wires.

The resistors as well as the wiring may consist of one or more non-ferromagnetic materials. In particular materials containing iron or nickel can be avoided in this way.

According to a further embodiment of the invention, the ultrasonic transducer, the resistor, as well as the twisted-wire wiring may be arranged on a non-ferromagnetic circuit board, which accordingly should be devoid of iron or nickel. Through such a circuit board, the automatable production may be facilitated. Additionally, a reliable arrangement of multiple elements can be ensured.

According to an embodiment of the invention, the ultrasonic transducer and the resistors in the housing of the ultrasonic sensor may be connected through a CTG cable with a CTG electronic system of the CTG device, which may be arranged remotely from the MRT. The CTG electronic system may be located a few meters from the MRT, for example in a separate room. According to an embodiment of the invention, the CTG cable between the ultrasonic sensor and the CTG electronic system can be longer than 5 m, for example 8 m.

In an embodiment of the invention, the CTG cable may be composed of a bipolar signal transmission core which has an inner shielding and an outer shielding, i.e., a double shielding. According to an embodiment, the inner shielding can be connected to a ground terminal of the CTG electronic system or a ground terminal of the CTG device. According to an embodiment, the outer shielding can be connected to a ground terminal of the MRT.

Further, the inner shielding may be connected to a housing shield which is located within the housing of the ultrasonic sensor. The housing shield can be a shield film of copper or a metallization of the inner surface of the housing.

As an additional shield the housing of the ultrasonic sensor may be completely metalized on the outside, e.g., treated with conductive silver. On the housing of the ultrasonic sensor, the additional shield or the conductive silver may be connected to the outer shielding of the CTG cable, whereby the outer shielding of the CTG cable in turn may be connected to the ground terminal of the MRT.

According to a further embodiment of the invention, at least one ferrite core, e.g. in the form of a ferrite ring, is arranged around the CTG cable.

According to a further embodiment of the invention, also wireless transmission can be provided. For example, by means of a transmitter/receiver unit, the ultrasonic sensor may perform wireless signal transmission between the ultrasonic sensor and the CTG electronic system. Further, it is also possible that the CTG electronic system is integrated in the housing of the ultrasonic sensor, and by means of a transmitter unit an output signal of the CTG electronic system, representing a heart rhythm, may be transmitted wirelessly to the MRT, which for example may use it as trigger signal for heart imaging. If the CTG electronic system is integrated with the ultrasonic sensor in the same housing, preferably also the CTG electronic system is realized with nonferromagnetic materials and uses a wiring with twisted-pair cables to avoid disturbances by dynamic electric and magnetic fields in operation of the MRT. Further, in this case the CTG electronic system may also comprise signal filters for suppressing frequencies of the high-frequency signals irradiated by the MRT.

Each of the above-described separate shielding measures provides for an improved compatibility of the ultrasonic sensor with the MRT.

According to a further embodiment of the invention, the ultrasonic sensor according to one or more of the above-mentioned embodiments may be used together with a CTG electronic system and an MRT, whereby the ultrasonic sensor is arranged within the magnetic field of the MRT and whereby the imaging of the MRT is controlled (triggered) by an output signal of the CTG electronic system (or a signal of the ultrasonic sensor).

According to a further embodiment of the invention, a system for imaging of a heart, in particular a fetal heart, is provided, which comprises an ultrasonic sensor, a CTG electronic system or a CTG device, and an MRT, whereby the CTG electronic system is adapted to provide, on the basis of oscillation detection by the ultrasonic transducer, a signal for controlling imaging by the MRT.

For this purpose, the CTG electronic system may repeatedly send special pulse chains (bursts) to the sensor, which irradiates these as ultrasonic sound. Then the respective echo of the bursts may be received and interpreted by the CTG electronic system, whereby the interpretation in this application may be based on runtime differences (Doppler effect), from which then the heart frequency can be calculated.

According to a further embodiment of the invention, the signal from the ultrasonic sensor to the CTG device or to an active CTG electronic system of the CTG device may also be wirelessly transmitted. For this purpose, the ultrasonic sensor may comprise a transmitter/receiver unit, which is arranged close to the ultrasonic sensor, but outside the MRT, so that wireless transmission between this transmitter/receiver unit and the CTG electronic system may be performed.

The above-described aspects and further aspects, features and advantages of embodiments of the invention may also be learned from the examples of embodiments, which in the following will be described with reference to the accompanying drawings.

DETAILED DESCRIPTION OF EMBODIMENTS

Figure 1:
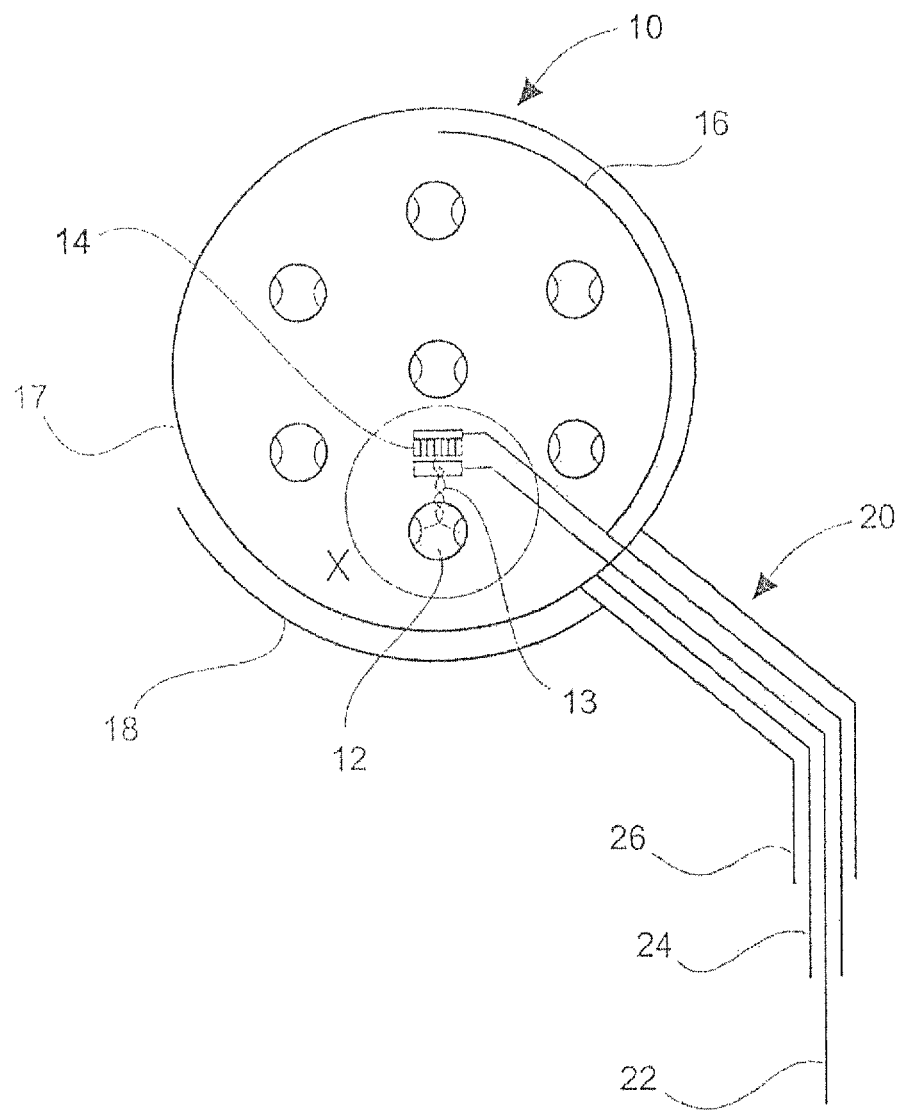
FIG. 1 is a schematic illustration of an ultrasonic sensor according to an embodiment of the invention.

FIG. 1 shows a schematic illustration of an ultrasonic sensor 10 with a CTG cable 20 according to an embodiment of the invention. The ultrasonic sensor provides a trigger signal for improved imaging by an MRT.

The ultrasonic sensor 10 has a housing 17 in which an ultrasonic transducer 12 and resistors 14 are located. By way of example, in FIG. 1 an ultrasonic transducer 12 and a resistor 14 are connected to each other through a twisted wiring 13 (detail X). For the sake of overview, it was refrained from depicting the twisted wirings between the other ultrasonic transducers and the corresponding resistors.

Further, a shield film 16 is provided within the housing 17. In FIG. 1, the shield film 16 is only indicated schematically. It is noted that the shield film may be configured in such a way that it covers all ultrasonic transducers 12 and also the resistors 14 and the wirings 13 within the housing 17.

The exterior of the housing 17 is completely metalized, for example treated with conductive silver 18. Also in this case, the conductive silver 18 is only partially and schematically indicated in FIG. 1. It is noted that the conductive silver 18 may cover the complete outer surface of the housing 17.

A CTG cable 20 extends from the housing 17 of the ultrasonic sensor 10. The CTG cable 20 is composed of a core 22, an inner shielding 24, and an outer shielding 26. Within the ultrasonic sensor, the inner core 22 is connected to the wiring 13 of the resistors 14 and the ultrasonic transducers 12, so that the signal from the ultrasonic transducers can be conducted from the ultrasonic sensors to a CTG electronic system. The core of the CTG cable 20 may have a bipolar configuration.

On the side of the ultrasonic sensor, the inner shielding 24 extends into the housing 17 and, in the housing, is connected to the shield film 16. The inner shielding 24 is provided over the entire length of the cable 20 and, at its other end, is connected to the ground terminal of the CTG electronic system. In this way, the shield film in the housing 17 of the ultrasonic sensor is connected to the ground terminal of the CTG electronic system.

The outer shielding 26 of the CTG cable 20 is not provided over the entire length of the CTG cable. For example, 1.5 m of the CTG cable starting from the ultrasonic sensor 10 may be formed with the outer shielding 26. This additional outer shielding is connected to the ground terminal of the MRT and, on the ultrasonic sensor, connected to the conductive silver 18 on the outside of the housing 17.

Figure 2:
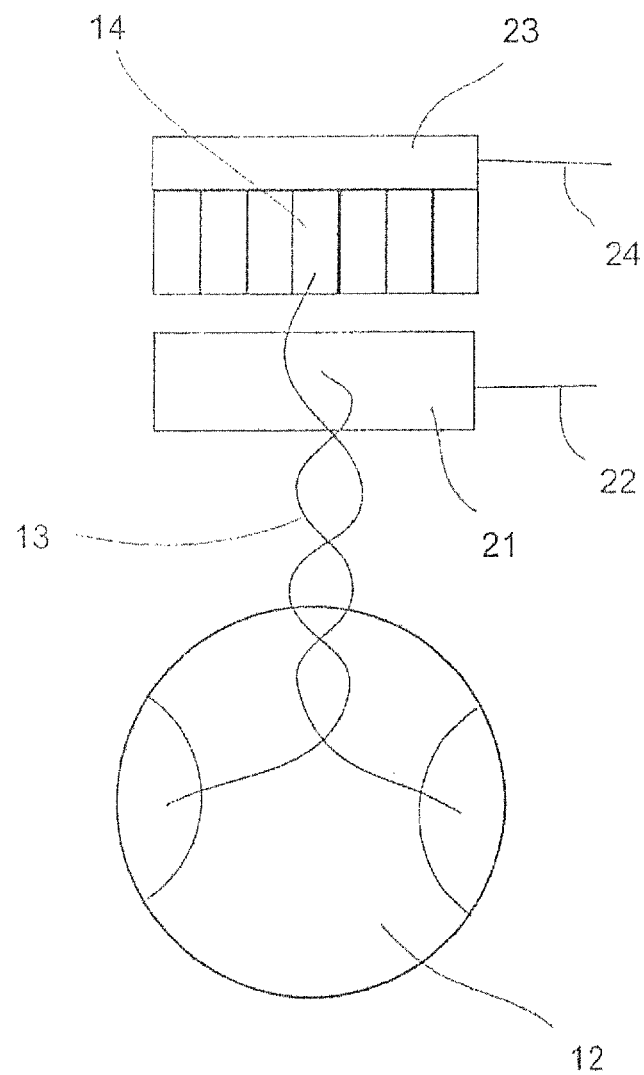
FIG. 2 is an enlarged illustration of detail X in FIG. 1.

FIG. 2 shows detail X in FIG. 1 in an enlarged illustration. Via twisted wiring 13, the ultrasonic transducer 12 is connected on the one hand to the core 22 of the CTG cable as signal conductor and on the other hand via a resistor 14 to the inner shielding 24 of the CTG cable. The resistor 14 forms a part of a block which is composed of seven SMD-resistors, whereby these seven resistors have a common resistor contatct 23 to the shielding 24 and each a respective free contact.

One of the two wires 13 coming from the ultrasonic transducer 12 is connected to a free contact of a resistor 14, and the other of the two wires is connected to the core 22, whereby signal contact point 21 is formed in such a way that all ultrasonic transducers may be connected to this contact point.

Figure 3:
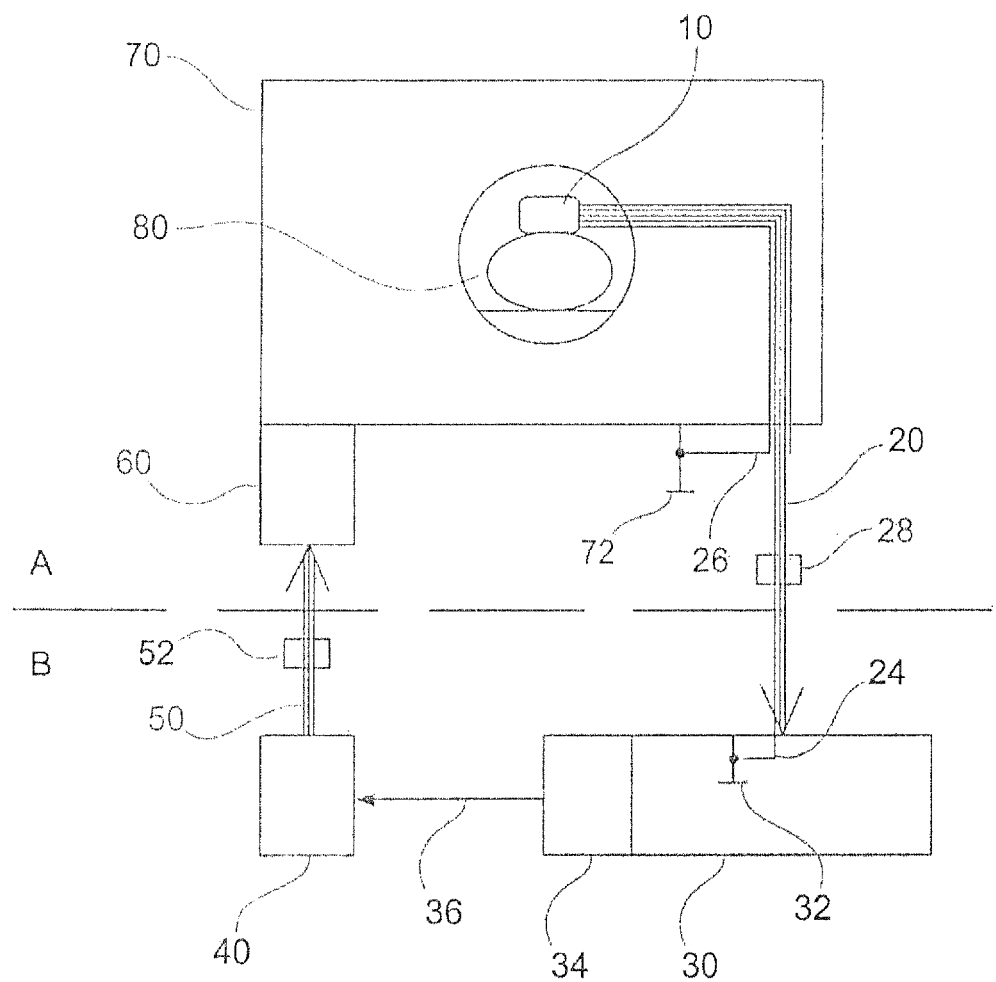
FIG. 3 is a schematic illustration of a system with CTG and MRT according to the invention.

FIG. 3 shows a schematic illustration of a system for imaging of a heart, in particular a fetal heart, according to an embodiment of the invention. The ultrasonic sensor 10 is connected via the CTG cable 20 with a CTG electronic system 30. Also here in FIG. 3, it is indicated that the inner shielding 24 of the cable 20 is connected to the ground terminal 32 of the CTG electronic system 30. Further, it is illustrated that the outer shielding 26 is connected to the ground terminal 72 of the MRT 70. Further, it is illustrated that a ferrite core 28, in the form of a ferrite ring, is arranged around the CTG cable 20.

On the CTG electronic system 30, an illumination field in the front plate may blink in the heart rhythm, as in a conventional CTG device. To utilize this blinking illumination field, an optocoupler 34 may be used, which generates an electronic signal, representing a heart rhythm, from the signal of the illumination field. Alternatively, it is possible to use a CTG device which provides an electric output signal representing a heart rhythm. Finally, the CTG electronic system 30 may also be integrated in the same housing with the ultrasonic sensor 10, e.g. in the form of a handheld device. In this case, also a wireless transmission of the output signal of the CTG electronic system 30 may be transmitted to the MRT 70, e.g. via radio signals, infrared signals or acoustic signals.

In the illustrated example, the electronic signal of the optocoupler 34 is forwarded via a cable 36 to an electronic circuit 40, which converts the signal into a ECG-like, very low impedance signal. Via coaxial cable 50, on which a further ferrite core 52 may be provided, this converted signal is forwarded to a further electronic circuit 60, which accomplishes signal level adaptation.

The resulting conditioned signal may now be used by the MRT 70 as control signal (trigger signal) for heart imaging. In this way, MRT visualizations of the heart of a patient 80 may be performed, which are always recorded at the same point of time in a heart cycle, so that anatomic structures of the heart may be visualized at very high resolution. By means of the system according to the illustrated embodiment of the invention, this is in particular also possible for a heart of an unborn child in the mother's womb. It is noted that also the course of heart movement may be visualized, whereby for this purpose the control signal may determine, relative to the heart cycle, a progressing point of time for imaging.

It is to be understood that various modifications are possible in the illustrated embodiments. For example, the ultrasonic sensor and the CTG electronic system do not need to be provided as separate components, but may be integrated in the same housing, e.g., the housing 17 of the ultrasonic sensor 10 as illustrated in FIG. 1. For example, the ultrasonic sensor and the CTG electronic system may be combined in a handheld device or compact device. Also the required hardware and software for signal generation and conditioning could then be implemented in this compact device, which may be configured in an MRT compatible manner, similar to the ultrasonic sensor. The MRT compatible compact device may for example be placed on the patient above the object the be examined, and the measured signals may be wirelessly forwarded to the MRT. A special CTG cable, e.g. with ground shunt at the MRT device, may then be dispensed with.

Further, it is to be understood that the concepts as described herein offer advantages in a plurality of application fields. Examples of such application fields are:

Generation of a trigger signal which represents the heart frequency of adults, children or fetuses in utero. This trigger signal may be used for heart and vessel imaging in the MRT. The triggered cardiovascular fetal MRT imaging, which is enabled in this way, delivers valuable information for the further therapeutic action in case of fetal malformations. The MRT allows for a precise anatomic visualization of the heart (including foramen ovale) and additionally functional conclusions, such as for example the ejection fraction. Thus, the degree of a cardiac malformation may be determined already in utero for planning subsequent surgical interventions. Apart from application in prenatal diagnostics, the system may also replace the ECG control in the examination of adults. It may then be utilized in a beneficial manner for examination of adults, if the conventional ECG electrodes generally cause additional efforts (shaving the chest) and problems (falling off of the self-adhesive electrodes) and are impossible to be applied in some cases (e.g. with patients having pleural effusions, pericardial effusions, adiposity).

Monitoring the heart frequency of fetuses, children, adults, and thus a vital function, during the MRT measurement: Beside the cardiac triggering, the MRT compatible CTG device described herein is also applicable for continuous monitoring of fetuses during MRT examination. This is of clinical relevance because often high-risk pregnancies are examined in MRT. Of course such monitoring may also be performed on children or adults.

The invention claimed is:

1. An ultrasonic sensor for cardiotocography within a magnetic field of a magnetic resonance tomography (MRT) system, comprising:
   at least one ultrasonic transducer,
   at least one resistor, and
   a housing configured to be arranged within the magnetic field, wherein the housing accommodates:
      the at least one ultrasonic transducer,
      the at least one resistor, and
      a cardiotocography electronic system comprising a circuitry configured to provide an output signal representing a heart frequency of a fetus, wherein the cardiotocography electronic system outputs a signal that is configured to trigger signal for heart imaging by the MRT system,
      wherein the circuitry of the cardiotocography electronic system is configured to process the output signal within the magnetic field,
   wherein the ultrasonic sensor is formed of a non-ferromagnetic material, and wherein the at least one resistor and the at least one ultrasonic transducer are connected to each other through twisted wires.

2. Ultrasonic sensor according to claim 1, further comprising a cable for connecting the at least one ultrasonic transducer and the at least one resistor to a cardiotocography electronic system, wherein the housing further comprises a shield film, and wherein the cable comprises an inner shielding for connecting the shield film to a ground terminal of the cardiotocography electronic system.

3. Ultrasonic sensor according to claim 2, wherein the housing is provided with a metallization on the outside, and wherein the cable comprises an outer shielding for connecting the metallization to a ground terminal of an MRT.

4. Ultrasonic sensor according to claim 2, wherein a ferrite ring is arranged around the cable.

5. Ultrasonic sensor according to claim 1, comprising:
a transmitter unit for wireless transmission of the output signal to a magnetic resonance tomograph.

6. Ultrasonic sensor according to claim 1, wherein the cardiotocography electronic system includes signal filters configured to suppress high frequency signals generated by the MRT system.

7. Ultrasonic sensor according to claim 1, wherein the cardiotocography electronic system is further configured to:
receive an echo from the at least one ultrasonic transducer, and
interpret the received echo to determine the heart frequency based on a Doppler effect present in the received echo.

* * * * *